United States Patent [19]

Burton et al.

[11] 4,049,383
[45] Sept. 20, 1977

[54] METHOD OF DETECTING GASEOUS CONTAMINANTS

[75] Inventors: C. Shepherd Burton, San Rafael; Alan B. Harker; William W. Ho, both of Thousand Oaks, all of Calif.

[73] Assignee: Rockwell International Corporation, El Segundo, Calif.

[21] Appl. No.: 757,277

[22] Filed: Jan. 6, 1977

[51] Int. Cl.$^2$ ..................... G01N 21/58; G01N 21/26
[52] U.S. Cl. ................................ 23/232 E; 23/232 R; 23/254 E
[58] Field of Search ............. 23/232 R, 232 E, 254 R, 23/254 E, 255 R; 73/23

[56] References Cited

U.S. PATENT DOCUMENTS

| | | | |
|---|---|---|---|
| 3,420,636 | 1/1969 | Robbins | 23/254 R |
| 3,545,931 | 12/1970 | McKinley, Jr. | 23/232 R |
| 3,562,128 | 2/1971 | Coffey | 23/232 R X |
| 3,904,371 | 9/1975 | Neti et al. | 23/232 R |
| 3,977,836 | 8/1976 | Matsuda et al. | 23/232 E |

OTHER PUBLICATIONS

Harker et al., "A Kinetic Study of the Mercury Sensitized Luminescence of H$_2$O and NH$_3$," Jour. of Chem. Phy., vol. 63, No. 2, (1975).

Primary Examiner—R.E. Serwin
Attorney, Agent, or Firm—L. Lee Humphries; Henry Kolin; Clark E. DeLarvin

[57] ABSTRACT

A method for the detection and quantitative analysis of certain selected constituent parts of a gas stream. A gas stream containing the selected constituent is introduced into a reaction zone and contacted with metastable mercury (6$^3$P$_o$) atoms to form an excited complex of the selected constituent and the metastable mercury atom, which decomposes emitting light. The intensity of the light emission is measured and directly correlatable to the concentration of the constituent in the gas stream. The method of the present invention is particularly applicable to the measurement of ambient air containing selected constituents in an amount or concentration in the 1-100 ppb range. The method can be used to measure trace amounts of numerous selected constituents contained in a gaseous stream including such constituents as ammonia, hydrazine, water vapor, alcohols and various amines.

10 Claims, 3 Drawing Figures

METHOD OF DETECTING GASEOUS CONTAMINANTS

BACKGROUND OF THE INVENTION

1. Field of the Invention

The present invention relates to the measurement of component parts of a gaseous stream. It particularly relates to the measurement of certain selected constituents of a gas which are present in only trace amounts.

2. Prior Art

In recent years there has been a considerable interest in the quality of our environment, particularly with respect to the effects of air pollution on health. Recent studies have indicated that even trace amounts of certain pollutants could have adverse health effects. For example, recent studies indicate that gaseous ammonia plays a significant role in the formation and stabilization of aerosol particles in a polluted atmosphere, and these particles can potentially cause adverse health effects. Ambient ammonia generally is present in the atmosphere in the parts per billion range. While there are numerous methods for measuring ammonia, most existing methods are not sufficiently sensitive to measure ambient ammonia at such low concentrations or are not amenable to continuous monitoring.

There are, for example, wet chemical methods of measuring ammonia which utilize established techniques and relatively inexpensive hardware. However, wet chemical methods are subject to strong negative interference from formaldehyde, which is known to be present in the atmosphere in concentrations equal to or exceeding the nominal ammonia concentration. Attempts to minimize such interference have not been altogether satisfactory. In addition, wet chemical methods are not suitable for real time analysis or continuous monitoring.

The spectroscopic technique provides for direct measurement in real time. However, this technique is subject to strong interference by the presence of other constituents which also are present in the atmosphere, frequently in greater concentrations than, for example, ammonia. In addition, to obtain reliable analysis in the low parts per billion concentration requires a skilled technician. Another disadvantage is that the equipment is expensive.

Another potential method for ammonia measurement is chemiluminescence. The chemiluminescence method relies on measuring ammonia by converting it to nitrogen oxide. However, the ambient nitrogen oxide concentration is much larger than the ambient ammonia concentration. The accuracy and reliability of this method, therefore, is limited and strongly influenced by small fluctuations in the ambient nitrogen oxide concentration.

Obviously, there is a need for an improved method for determining the concentration of trace constituents in a gaseous stream such as ambient air.

SUMMARY OF THE INVENTION

In accordance with the method of the present invention there is provided a method of measuring the concentration of a selected constituent of a gas stream containing said constituent in trace amounts of less than about 10 ppm. Broadly, the invention comprises passing the gas mixture through a gas separation means to separate the gas into its various constituent parts, which are then sequentially introduced into a reaction zone and reacted with metastable mercury atoms to form an excited mercury-selected constituent complex. The complex decays or decomposes emitting light having a wavelength characteristic of that particular complex. The intensity of the emission resulting from the decay of the excited mercury-selected constituent complex is measured and from that intensity the concentration of the selected constituent determined.

In accordance with a preferred method of practicing the present invention, methanol vapors are introduced into the reaction zone continuously or at intermittent times. When monitoring ambient air, for example, the sensitivity of the method decreases with time, caused by reaction product buildup in the reaction zone. However, the methanol vapors act as a gas-phase scavenger maintaining system cleanliness, and the system's sensitivity can be maintained for indefinite periods of time. The inventors do not wish to be bound by any particular theory, but it is believed that the methanol scrubs the walls of the reaction zone removing interfering contaminants which accumulate thereon.

DESCRIPTION OF A PREFERRED EMBODIMENT

Figure 1:
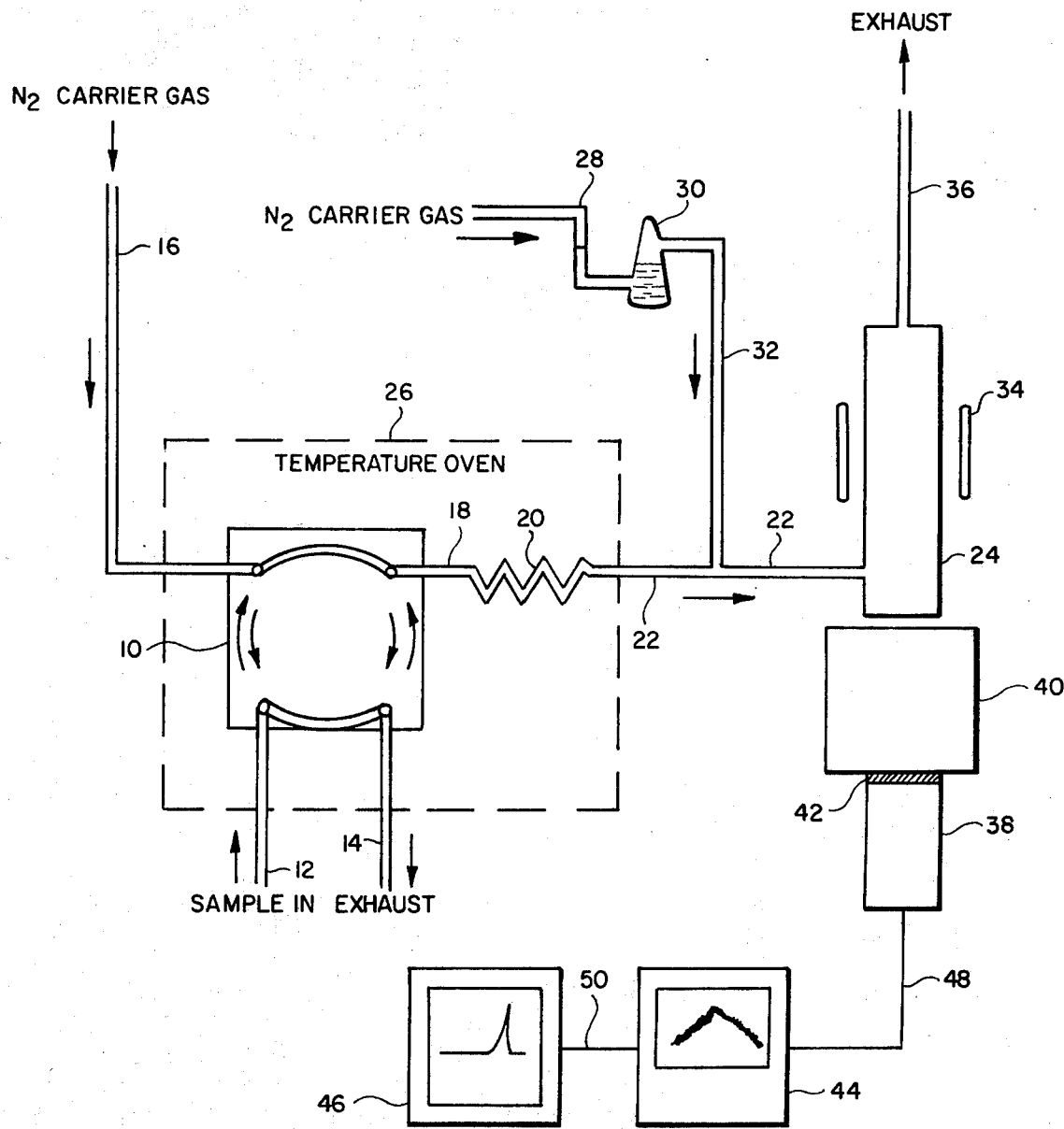
FIG. 1 is a schematic of a system for practicing the method of the present invention.

There frequently is need of a method for measuring the concentration of trace constituents in a gas stream. The present invention provides such a method. A sample of a gaseous mixture containing a selected constituent of interest is separated into its various constituent parts, for example, by passing the gas mixture through a gas chromatographic column. The various constituent parts then are sequentially introduced into a reaction zone where they are reacted with metastable mercury ($6^3P_o$) atoms to form an excited or unstable mercury-selected constituent complex. The method of the present invention is based on the observation of the emission intensity resulting from the decay of the excited mercury-constituent complex. The emitted light is in a band centered about a wavelength which is characteristic of the particular mercury-selected constituent complex. The concentration of the selected constituent in the gas sample is readily determinable as a function of the intensity of the light emission.

A variety of compounds form light emitting unstable or excited compounds with metastable mercury atoms. A representative list of such compounds and the characteristic emission wavelength resultant from the decomposition or decay of the mercury complex are set forth in the table below.

| SPECIES | CHARACTERISTIC EMISSION WAVELENGTH (nm) |
| --- | --- |
| water | 285 |
| ammonia | 345 |
| hydrazine (produces ammonia exciplex) | 345 |
| methanol | 295 |
| ethanol | 300 |

-continued

| SPECIES | CHARACTERISTIC EMISSION WAVELENGTH (nm) |
|---|---|
| n-propanol | 300 |
| iso-propanol | 302 |
| n-butanol | 298 |
| isobutanol | 297 |
| tert-butanol | 301 |
| tert-amyl alcohol | 303 |
| methyl amine | 355.5 |
| ethyl amine | 359.5 |
| n-propylamine | 360 |
| isopropylamine | 354.5 |
| n-butylamine | 360 |
| iso-butylamine | 360.5 |
| sec-butylamine | 361.5 |
| tert-butylamine | 359 |

It must be appreciated that the foregoing list is only representative of the various compounds or constituents which are measurable in accordance with the present method. For convenience the method of the present invention will be described with reference to a constituent of particular interest, namely, ammonia.

It was known heretofore that metastable mercury formed an excited complex with various constituents such as ammonia in the gas phase which decays via the emission of light. See, for example, "A Kinetic Study of the Mercury Sensitized Luminescence of $H_2O$ and $NH_3$" by Alan B. Harker and C. Shepherd Burton, *The Journal of Chemical Physics,* Vol. 63, No. 2, (1975) and reference cited therein.

The metastable-mercury atoms are created by the quenching (usually with nitrogen) of mercury in the $(6^3P_1)$ state, which latter state is produced by irradiating mercury vapor with 253.7 nm light. The hypothesized mechanism for the formation and decay of the mercury complex are given by the following exemplary reactions, wherein M is any other gas species present other than Hg, $NH_3$, or $N_2$.

(1) $Hg + h\nu\ (253.7\ nm) \rightarrow Hg(6^3P_1)$
(2) $Hg(6^3P_1) + N_2 \rightarrow HG(6^3P_o) + N_2{}^*$
(3) $Hg(6^3P_o) + NH_3 \rightarrow (Hg\cdot NH_3)^*$
(4) $Hg(6^3P_o) + NH_3 + N_2 \rightarrow (Hg\cdot NH_3)^* + N_2$
(5) $(Hg\cdot NH_3)^* \rightarrow Hg + NH_3 + h\nu\ (345.0\ nm)$
(6) $(Hg\cdot NH_3)^* + N_2 \rightarrow Hg + NH_3 + N_2$
(7) $(Hg\cdot NH_3)^* + M \rightarrow Products$
(8) $Hg(6^3P_o) + N_2 \rightarrow H_g + N_2{}^*$
(9) $Hg(6^3P_o) + M \rightarrow Hg + M^*$
(10) $Hg(6^3P_1) + M \rightarrow Hg + M^*$

*indicates an excited or unstable form

The light emission intensity of the complex is directly proportional to the ammonia concentration. The overall sensitivity is a function of the magnitude of certain rate constants, incident excitation light intensity and the level of impurities or M gases existing in the reaction cell. Thus, for a given set of operating conditions and for a constant level of trace contaminants, the emission intensity provides a simple measure of ammonia concentration.

The presence of impurities in the system will influence the observed ammonia-metastable mercury complex emission via the quenching reactions (9) and (10) above, which reduce the steady state concentration of the $Hg(6^3P_1)$ and $Hg(6^3P_o)$ atoms necessary for the formation of the desired complex of reaction (5). To obtain a high degree of sensitivity and accuracy it has been found certain contaminant gases must be maintained at a low level. Specifically, the allowable concentration for some common gases are less than 2 ppm of $O_2$, less than about 6.5 ppm of $H_2$, less than about 1.5 ppm of NO, less than about 34 ppm of CO, less than 3000 ppm of $C_2H_6$ and less than about 0.8 ppm of $C_2H_4$.

When the gas stream being monitored is ambient air, molecular oxygen removal is by far the most critical problem in view of its significant quenching effect as well as the high concentration encountered in ambient air. Thus, the concentration of oxygen in a sample obtained from ambient air must be reduced by approximately a factor of $10^5$ in order to maintain the same detection sensitivity that would be achieved in measurements made with $NH_3$ in pure $N_2$. It should be noted, however, the presence of $O_2$ only decreases the sensitivity and does change the linearity of the emission intensity with $NH_3$ concentration so long as the $O_2$ concentration remains constant. Therefore, the degree to which $O_2$ can be tolerated is largely dependent on the desired sensitivity for a given application.

In the present method, the gas sample is first passed through a gas separation means such as a chromatographic column to separate the gas into its separate constituent parts which then are sequentially introduced into the reaction zone for reaction with metastable mercury, whereby the subsequent emission is monitored independently of that of the other constituents of the gas stream. Thus, the present method overcomes the potential loss in sensitivity which could result from the presence of any interfering contaminants.

An exemplary schematic of a system for use in accordance with the method of the present invention is depicted in FIG. 1. The apparatus includes a known or constant volume sample valve 10, which is in fluid communication with a sample inlet conduit 12 and a sample exhaust conduit 14. Also connected to sample valve 10 is a conduit 16 for the introduction of a carrier gas and a sample discharge conduit 18 for introducing the sample into a gas separation means 20, which typically will be a gas chromatographic column for separating the gaseous mixture into its separate constituent parts. The gas exits the separation means 20 via conduit 22 for introduction into a reaction zone defined by a cell 24. Advantageously, sample valve 10 and gas separation means 20 are maintained at a constant temperature preferably by locating them in a constant temperature oven 26.

A source of metastable mercury atoms is provided by introducing a carrier gas (preferably nitrogen) via conduit 28 into a container 30 of mercury to provide a mercury vapor saturated gas which exits container 30 via a conduit 32 for introduction into cell 24 via conduit 22. The reaction zone defined by cell 24 is exposed to a source of ultraviolet light 34 having a wavelength of about 253.7 nm, which typically is provided by a mercury lamp preferably provided with the desired wavelength filter. The gases are exhausted from cell 24 via a conduit 36.

Any emissions produced in cell 24 are monitored with a light emission detector means 38, which advantageously is provided with a filter means for blocking emission wavelengths other than those of interest. Typically, the filter means will include a monochromator 40 and, in addition, or alternatively thereto, a bandpass filter 42, so that only the wavelengths of interest may pass therethrough. An output from detector means 38 is introduced into a display means 44 and optionally a recorder means 46 via a line 48 and 50, respectively. It will be readily apparent to those versed in the art that several or all of these components could be combined in a single unit.

In operation, the gas continuously passes through sample valve 10 via conduits 12 and 14, and a sample of fixed volume is introduced into the chromatographic column 20 by actuating sample valve 10. The gas sample is then conveyed by the carrier gas, introduced via conduit 16 through sample conduit 18 into gas separation means 20 for separation into its respective constituent parts. The constituent parts then are sequentially introduced into the reaction zone defined by cell 24. Mercury vapors and nitrogen are conveyed from container 30 via conduit 32 and 22 for introduction into cell 24, where they are irradiated by the 253.7 nm light to produce unstable mercury ($6^3P_1$) atoms, which react with the nitrogen to form a metastable mercury ($6^3P_o$) atom. The metastable mercury atom combines with the selected constituent of interest is form an unstable or excited complex, which decays emitting light having a frequency characteristic of the metastable mercury-selected constituent complex. This light is then detected by detector 38, and the intensity thereof indicated on display means 44, and, if provided, on permanent recording means 46, thus providing a measurement which is correlatable to the concentration of the constituent in the gas sample.

EXAMPLE

The following example is set forth to further demonstrate the method of the present invention. The system utilized is substantially the same as that depicted in FIG. 1. Sample valve 10 and oven 26 were commercially purchased components, the sample valve being a standard micro volume sample valve (having a sample volume of 0.1 cc) and the oven selected to have a volume capable of housing the valve and gas separation means 20 and maintaining them at a desired temperature of about 80° C. Gas separation means 20 is a standard purchased gas chromatographic column comprising a 1.5 meter long, 0.23 cm O.D. teflon tube packed with 60–80 mesh chromatographic substrate which was treated with a 10% by weight solution of tetrahydroxyethylenediamene. The reaction zone defined by cell 24 comprised a 1.25 cm diameter by 5 cm long quartz tube with an optically flat window attached to one end. The source of ultraviolet radiation 34 was a commercial 253.7 nm mercury lamp. The light emission detector utilized was a photomultiplier tube with ultraviolet response provided with both a quarter meter monochromator and a 350 cm bandpass filter for the specific detection of the metastable mercury-ammonia complex. The output from the photomultiplier tube was fed into a commercial multi-channel analyzer capable of performing simultaneous real time as well as integrated time averaging sampling. The carrier gas utilized was an ultra-pure grade of nitrogen.

Using known volume samples of ammonia in nitrogen and ammonia in air, studies were made to demonstrate the utility of the system for ammonia concentration measurements as well as to determine any degradation of the measurement due to column effects, such as incomplete separation, and loss of material due to irreversible wall absorption.

Figure 2:
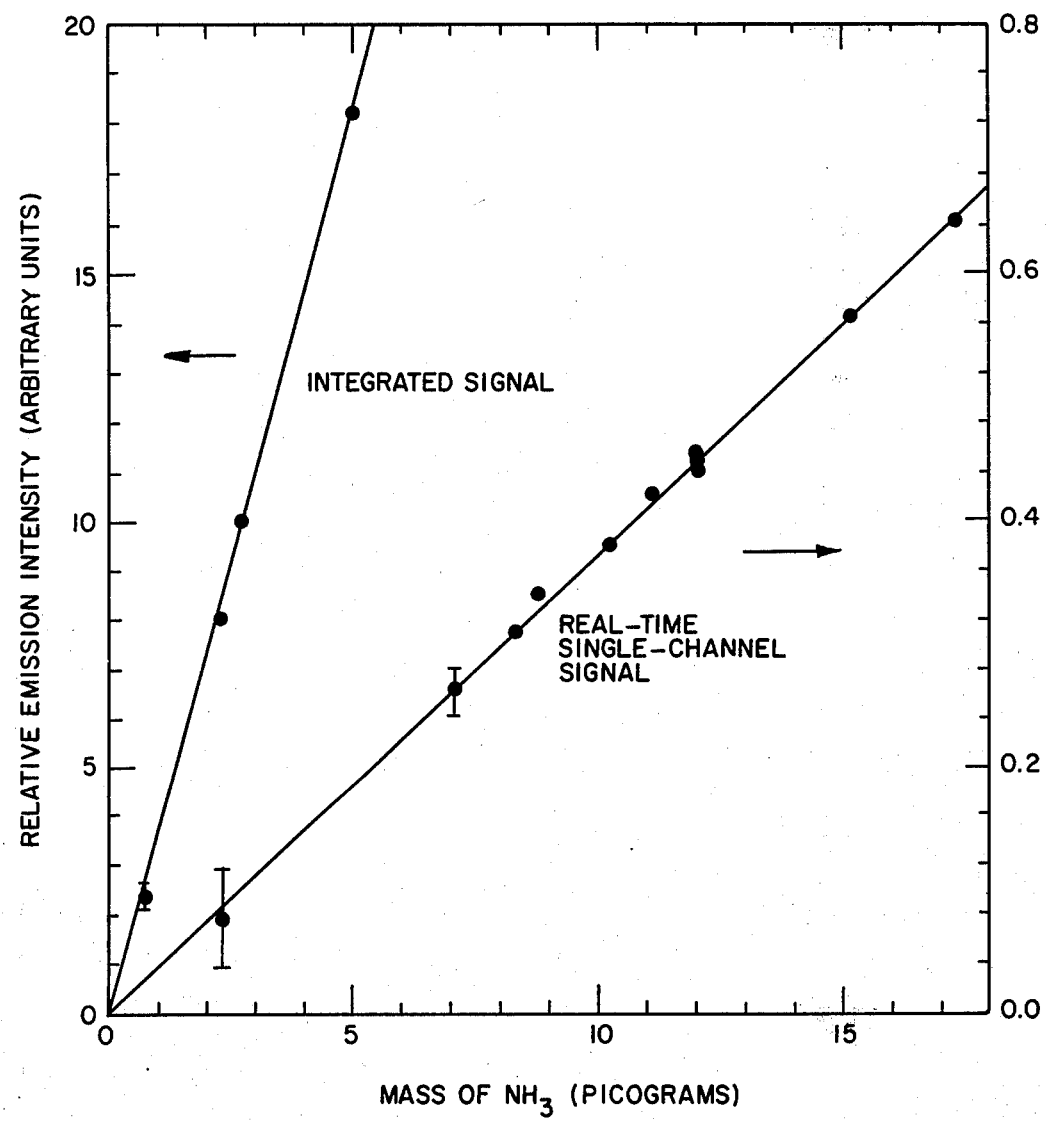
FIG. 2 is a chart depicting relative light emission intensity versus ammonia concentration for a real time signal and a time-integrated signal.

Typical data were obtained in one series of tests with the continuous flow of nitrogen, containing various concentrations of ammonia, through the cell and monitoring the change in intensity of emission therefrom. FIG. 2 shows the relative intensity of the signals detected as a function of ammonia concentrations. It will be seen that the signal is linear with regard to the mass of ammonia gas injected over the range of measurements. Further, it is seen that integration of the measured intensity over the residence time of the sample while flowing through the detector cell greatly enhances the sensitivity of the signal detected, thus, demonstrating that the present method is capable of accurate sensitive measurements of concentrations as low as a few tenths of a picogram.

Figure 3:
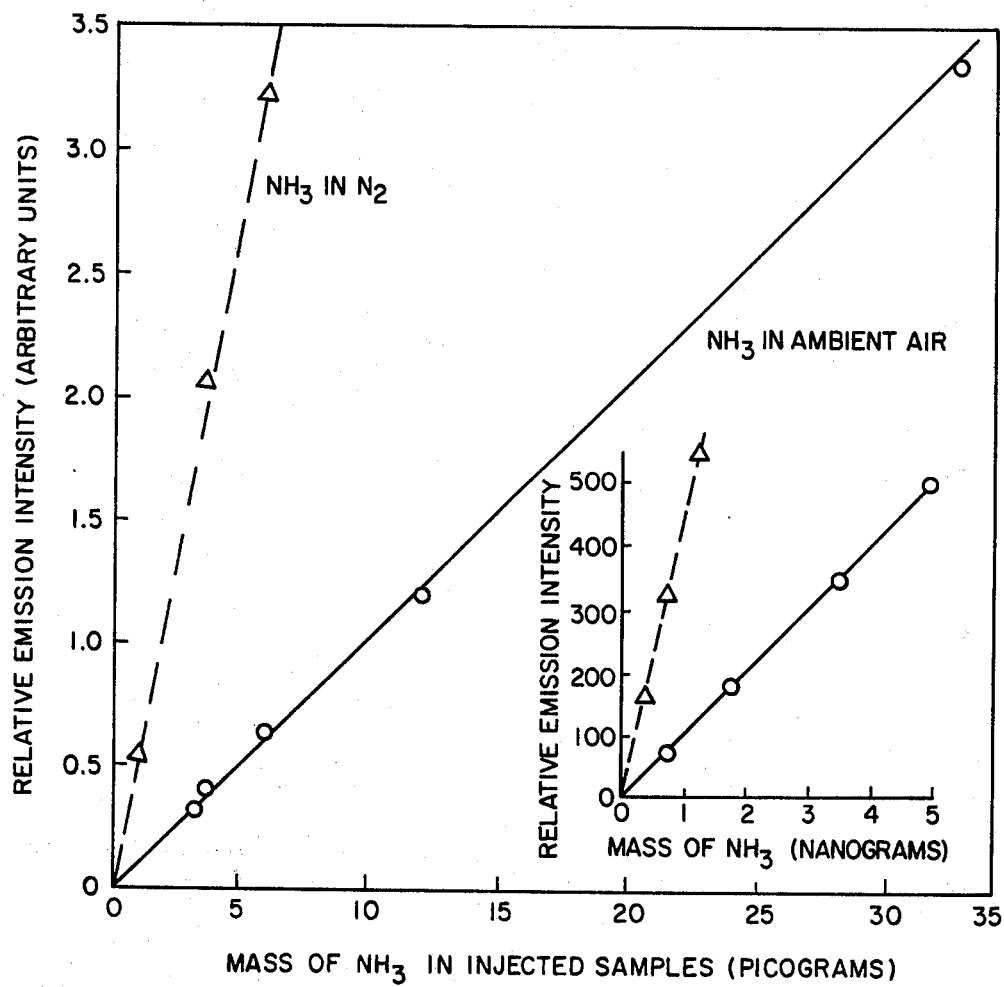
FIG. 3 is a chart depicting relative light emission intensity versus ammonia concentration in pure nitrogen and in ambient air.

Another extensive series of tests was carried out with the injection of ammonia in nitrogen and ammonia in ambient air through the chromatographic column. The relative integrated intensities obtained are shown in FIG. 3. It is seen that the signal is linear throughout the range tested. Indeed, the linearity was verified for ammonia concentrations up to 5000 picograms. The achieved sensitivity for samples of ammonia in air is about 3 picograms (with a signal-to-noise ratio of about 5), which corresponds to a detection limit on the order of 4 ppb in a 1 cc sample. Thus, the utility of the present method for measuring ambient concentrations of ammonia in the 1–100 ppb range is clearly established.

It will be understood, of course, that the above example was provided only to illustrate the invention. The invention may be practiced utilizing other equipment than that specifically described and may be utilized to test for the presence and concentration of constituent parts of gas streams other than those specifically illustrated. For example, different types of light emission detectors may be used for measurement and analysis, and gas separation means other than a gas chromatographic column may be used. In addition, the application of the present method to other gas streams containing a different constituent of interest is readily determinable by processing a sample of the constituent in an inert gas in accordance with the present method to determine if any emission is produced, its characteristic wavelength and to correlate that emission intensity with the concentration of the constituent.

Therefore, while the present invention has been described with respect to what at present are considered to be preferred embodiments thereof, it will be understood that changes, substitutions, modifications and the like may be made therein without departing from the scope of the invention as defined in the claims.

What is claimed is:

1. A method of measuring the concentration of a selected constituent of a gaseous mixture containing said constituent in amounts of less than about 10 ppm comprising the steps of:
    a. separating a sample of the gaseous mixture into its various constituent parts;
    b. sequentially introducing the constituent parts into a reaction zone and reacting said constituent parts with metastable mercury atoms to form an excited mercury-selected constituent complex, which decays emitting light having a characteristic wavelength;
    c. providing a light intensity measuring means for selective measurement of the light intensity of the characteristic wavelength emitted by decay of the mercury-selected constituent complex;
    d. measuring the intensity of the emission resulting from the decay of said excited mercury-selected constituent complex; and e. determining the concentration of the selected constituent as a function of said measured intensity.

2. The method of claim 1 wherein in step (a) said sample of the gaseous mixture is passed through a gas chromatographic column for separation into its various constituent parts.

3. The method of claim 1 wherein in step (b) said metastable mercury atoms are formed by irradiating mercury vapor with 253.7 nm light in the presence of nitrogen.

4. The method of claim 1 wherein the step (d) the intensity of the emission is measured and integrated over the residence time of the sample in the reaction zone.

5. The method of claim 1 wherein, intermediate the introduction of the samples of the gas mixture, methanol vapor is introduced into the reaction zone.

6. The method of claim 1 wherein said sample is atmospheric air.

7. The method of claim 6 wherein said selected constituent is ammonia.

8. The method of claim 7 wherein in step (a) said sample of the gaseous mixture is passed through a gas chromatographic column for separation into its various constituent parts.

9. The method of claim 8 wherein in step (b) said metastable mercury atoms are formed by irradiating mercury vapor with 253.7 nm light in the presence of nitrogen.

10. The method of claim 1 wherein said light intensity measuring means includes a photomultiplier tube, a monochromator and a bandpass filter.

* * * * *